(12) United States Patent
Chen

(10) Patent No.: US 11,019,849 B2
(45) Date of Patent: Jun. 1, 2021

(54) PUSH-BUTTON STRUCTURE AND ELECTRONIC ATOMIZER HAVING SAME

(71) Applicant: SHENZHEN IVPS TECHNOLOGY CO., LTD., Shenzhen (CN)

(72) Inventor: Wen Chen, Shenzhen (CN)

(73) Assignee: SHENZHEN IVPS TECHNOLOGY CO., LTD., Guangdong (CN)

( * ) Notice: Subject to any disclaimer, the term of this patent is extended or adjusted under 35 U.S.C. 154(b) by 611 days.

(21) Appl. No.: 15/870,955

(22) Filed: Jan. 14, 2018

(65) Prior Publication Data

US 2018/0160739 A1 Jun. 14, 2018

(30) Foreign Application Priority Data

Nov. 18, 2016 (CN) .......................... 201621247628.2

(51) Int. Cl.
| | |
|---|---|
| *A24F 47/00* | (2020.01) |
| *H05B 1/02* | (2006.01) |
| *A61M 15/06* | (2006.01) |
| *A61M 15/00* | (2006.01) |
| *H05B 3/00* | (2006.01) |
| *A61M 11/04* | (2006.01) |

(52) U.S. Cl.
CPC ....... *A24F 47/008* (2013.01); *A61M 15/0081* (2014.02); *A61M 15/06* (2013.01); *H05B 1/0227* (2013.01); *A61M 11/042* (2014.02); *A61M 2205/276* (2013.01); *A61M 2205/36* (2013.01); *H05B 3/00* (2013.01)

(58) Field of Classification Search
CPC ...................................................... A24F 40/49
See application file for complete search history.

(56) References Cited

U.S. PATENT DOCUMENTS

| | | | | |
|---|---|---|---|---|
| 4,504,707 | A | * | 3/1985 Ochiai ..................... H01H 3/20 200/43.17 |
| 2017/0099877 | A1 | * | 4/2017 Worm ................... A24F 47/008 |

* cited by examiner

*Primary Examiner* — Michael H. Wilson
*Assistant Examiner* — Katherine A Will
(74) *Attorney, Agent, or Firm* — IP-PAL Patent US; Klaus Michael Schmid

(57) ABSTRACT

The present disclosure provides a push-button structure. The push-button structure includes a support, a push-button, and a slide block. The push-button is connected to the support and has a push direction. The slide block is connected to the support in a sliding manner along a direction perpendicular to the push direction of the push-button, and the slide block is capable for sliding and has a locking position and an unlocking position. The push-button is provided with a first locking portion at one side facing the slide block. The slide block is provided with a second locking portion fitting the first locking portion. When the slide block slides to the locking position, the first locking portion is locked to the second locking portion. When the slide block slides to the unlocking position, the first locking portion is unlocked from the second locking portion.

8 Claims, 4 Drawing Sheets

PUSH-BUTTON STRUCTURE AND ELECTRONIC ATOMIZER HAVING SAME

CROSS REFERENCE TO RELATED APPLICATIONS

The present application claims priority to Chinese Patent Application CN 201621247628.2 filed on Nov. 18, 2016.

TECHNICAL FIELD

The present disclosure relates to the technical field of electronic atomizers, and particularly to a push-button structure and an electronic atomizer having the same push-button structure.

BACKGROUND

In the field of electronic cigarettes, many factories design a big area on the electronic cigarette into a push-button for smoking for the convenience of use. Thus, a push-button structure integrated into the electronic cigarette is formed. Since the push-button is relatively big, the push-button is easy to be pressed by other contact objects to cause an improper operation, while providing convenience for users.

At present, solutions for this problem available on the market are realized by software. The software sets a time interval. If no user pushes the push-button within the set time interval, the software locks the vapor system automatically. The software also sets a time interval between continuous pushing, and a number of times of pushing. When the push-button is pushed continuously and when both the time interval and the number of times of pushing reach set values, the vapor system is unlocked automatically. However, when the electronic cigarette is put in a pocket or bag, the push-button is easy to be pressed continuously by other contact objects to unlock automatically, thereby causing an improper operation.

SUMMARY

The present disclosure mainly aims to provide a push-button structure, so that an electronic atomizer having the same push-button structure can effectively prevent the impacts caused by improper operation of the push-button by manual execution of simple locking and unlocking operations.

In order to achieve the above aim, the present disclosure provides a push-button structure.

The push-button structure includes a support, a push-button, and a slide block.

The push-button is configured to be connected to the support and have a push direction.

The slide block is configured to be connected to the support in a sliding manner along a direction perpendicular to the push direction of the push-button, and the slide block is capable for sliding and has a locking position and an unlocking position.

The push-button is provided with a first locking portion at one side facing the slide block. The slide block is provided with a second locking portion fitting the first locking portion.

When the slide block is located at the locking position, the first locking portion is locked to the second locking portion; and when the slide block is located at the unlocking position, the first locking portion is unlocked from the second locking portion.

Preferably, the slide block is arranged at one side the push-button in the push direction.

The first locking portion includes a first protrusion portion projecting in the direction towards the slide block, and the second locking portion includes a second protrusion portion projecting in the direction towards the push-button.

When the slide block is located at the locking portion, the first protrusion portion has an end surface abutted against an end surface of the second protrusion portion; and when the slide block is located at the unlocking position, the first protrusion portion is staggered from the second protrusion portion.

Preferably, the slide block defines two locating grooves at one side far away from the second protrusion portion, and the two locating grooves are arranged spaced apart from each other along the slide direction of the slide block.

The support is provided with an elastic locating protrusion fitting the locating groove, and the slide block is abutted against the elastic locating protrusion in a sliding manner.

When the slide block is located at the locking position, the elastic locating protrusion is accommodated in one locating groove; when the slide block is located at the unlocking position, the elastic locating protrusion is accommodated in the other locating groove.

Preferably, the push-button structure further includes an elastic sheet fixed on the support, and the elastic sheet is provided with the elastic locating protrusion.

Preferably, the support defines a recess, an elastic element is arranged in the recess, the elastic element has one end abutted against a bottom wall of the recess and the other end abutted against the elastic locating protrusion.

Preferably, the elastic locating protrusion is a steel ball.

Preferably, each of the first protrusion portion and the second protrusion portion is provided with an arc transitional surface configured for connecting one side surface thereof to the end surface thereof; when the slide block is located at the unlocking position, the arc transitional surface of the first protrusion portion and the arc transitional surface of the second protrusion portion are configured to be arranged facing each other.

Preferably, the first locking portion defines an insert groove at one side thereof, and the second locking portion is provided with an insert element fitting the insert groove.

When the slide block is located at the locking position, the insert element is inserted into the insert groove; when the slide block is located at the unlocking position, the insert element is disengaged from the insert groove.

Preferably, the support further defines a mounting hole, the slide block is provided with a toggle portion, and the toggle portion is configured to extend out the mounting hole and slide in the mounting hole.

The present disclosure further provides an electronic atomizer. The electronic atomizer includes the push-button structure above.

According to the technical scheme of the present disclosure, the slide block slides relative to the support and has the locking position and the unlocking position. The slide block locks and unlocks the push-button when the slide block is located at the locking position and the unlocking position respectively, so that the push-button is in a locked state and an unlocked state. In the unlocked state, the push-button can be used normally. In the locked state, the first locking portion is locked to the second locking portion, which makes the push-button and the slide block fixed relative to each other. Since the slide direction of the slide block is perpendicular to the push direction of the push-button, the slide block cannot move along the push direction of the push-button. At such time, the push-button cannot move either, as a result, the push-button in such state is protected and the occurrence of improper operation is prevented. According to the push-button structure, the push-button is capable of switching between the locked state and the unlocked state by toggling the slide block manually. The mechanical operation is simple and reliable and can effectively prevent inconveniences caused by improper operation of the push-button.

BRIEF DESCRIPTION OF THE DRAWINGS

For a better understanding of the embodiments of the present disclosure or the technical scheme in the prior art, accompanying drawings needed in the description of the embodiments or the prior art are simply illustrated below. Obviously, the accompanying drawings described below are some embodiments of the present disclosure. For the ordinary skill in the field, other accompanying drawings may be obtained according to the structure shown in these accompanying drawings without creative work.

Description of reference numbers

Figure 1:
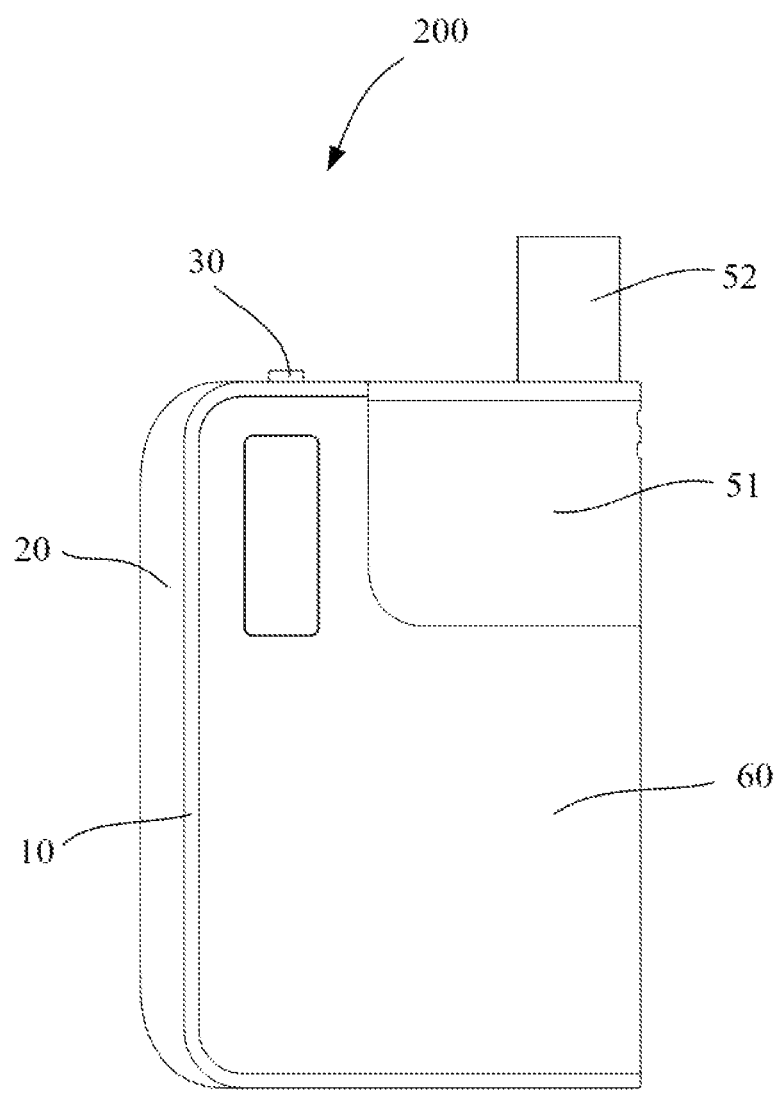
FIG. 1 is a structure diagram of an embodiment of an electronic atomizer of the present disclosure.

| Reference number | Part | Reference number | Part |
| --- | --- | --- | --- |
| 100 | Push-button structure | 313 | Locating groove |
| 10 | Support | 32 | Toggle portion |
| 11 | Mounting hole | 33 | Locking position |
| 20 | Push-button | 34 | Unlocking position |
| 21 | First locking portion | 40 | Elastic sheet |
| 211 | First protrusion portion | 41 | Elastic locating protrusion |
| 212 | First abutment surface | 50 | Mouthpiece assembly |
| 30 | Slide block | 51 | Mouthpiece base |
| 31 | Second locking portion | 52 | Mouthpiece |
| 311 | Second protrusion portion | 60 | Main body |
| 312 | Second abutment surface | 200 | Electronic atomizer |

The implementation of aims, the function features and the advantages of the present disclosure are described below in further detail in conjunction with embodiments with reference to the drawings.

DETAILED DESCRIPTION

A clear and complete description as below is provided for the technical scheme in the embodiments of the present disclosure in conjunction with the drawings in the embodiments of the present disclosure. Obviously, the embodiments described hereinafter are simply part embodiments of the present disclosure, but all the embodiments. All other embodiments obtained by the ordinary skill in the art based on the embodiments in the present disclosure without creative work are intended to be included in the scope of protection of the present disclosure.

It should be noted that all directional indications (such as top, bottom, left, right, front, behind . . . ) in the embodiments of the present disclosure are merely to illustrate a relative position relation, a relative motion condition, etc. between each part in a certain state (for example, the state shown in the drawings). If the state changes, the directional indication changes accordingly.

In the present disclosure, unless otherwise specifically stated and defined, terms "connected", "fixed", etc. should be interpreted expansively. For example, "fixed" may be fixed connection, also may be detachable connection, or integration; may be mechanical connection, also may be electrical connection; may be direct connection, also may be indirect connection through an intermediate, and may be internal communication between two elements or interaction of two elements, unless otherwise specifically defined. The ordinary skill in this field can understand the specific implication of the above terms in the present disclosure according to specific conditions.

In addition, if terms "first", "second", etc. appear in the present disclosure, they are merely for the purpose of description, but cannot be understood as the indication or implication of relative importance or as the implicit indication of the number of the designated technical features; therefore, features defined by "first" and "second" may specifically or implicitly include at least one such feature. In addition, technical schemes of each embodiment of the present disclosure may be combined mutually; however, this must be carried out on the basis that the ordinary skill in this field can implement the combination. When the combination of technical schemes has a conflict or cannot be implemented, it should be considered that such combination of technical schemes does not exist and is not in the scope of protection claimed by the present disclosure.

The present disclosure provides a push-button structure 100.

Figure 6:
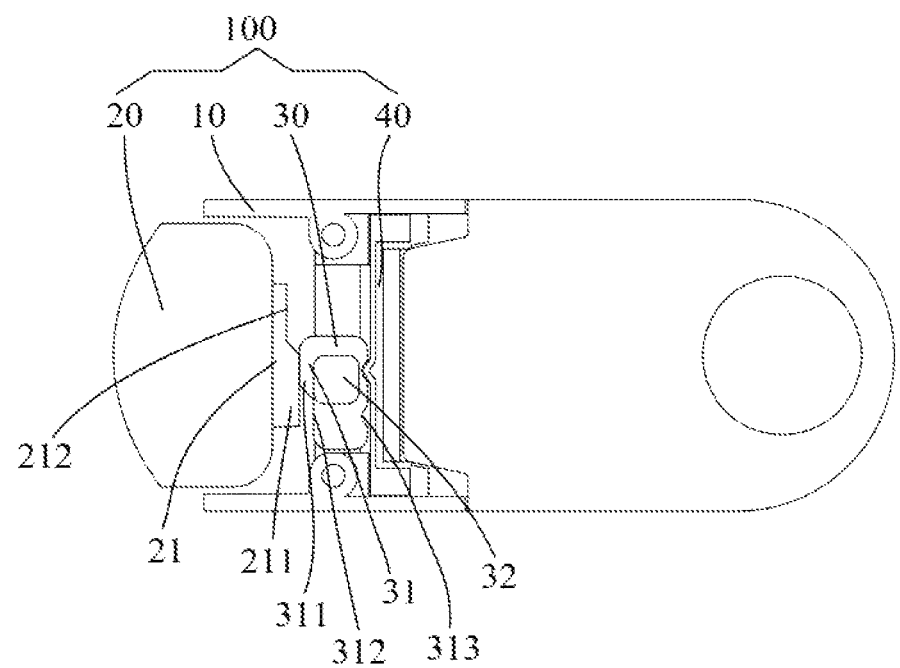
FIG. 6 is a partial cross-sectional view of an electronic atomizer shown in FIG. 5.

Referring to FIG. 6, the push-button structure 100 includes a support 10, a push-button 20, and a slide block 30.

The push-button 20 is configured to be connected to the support 10 and has a push direction.

Figure 3:
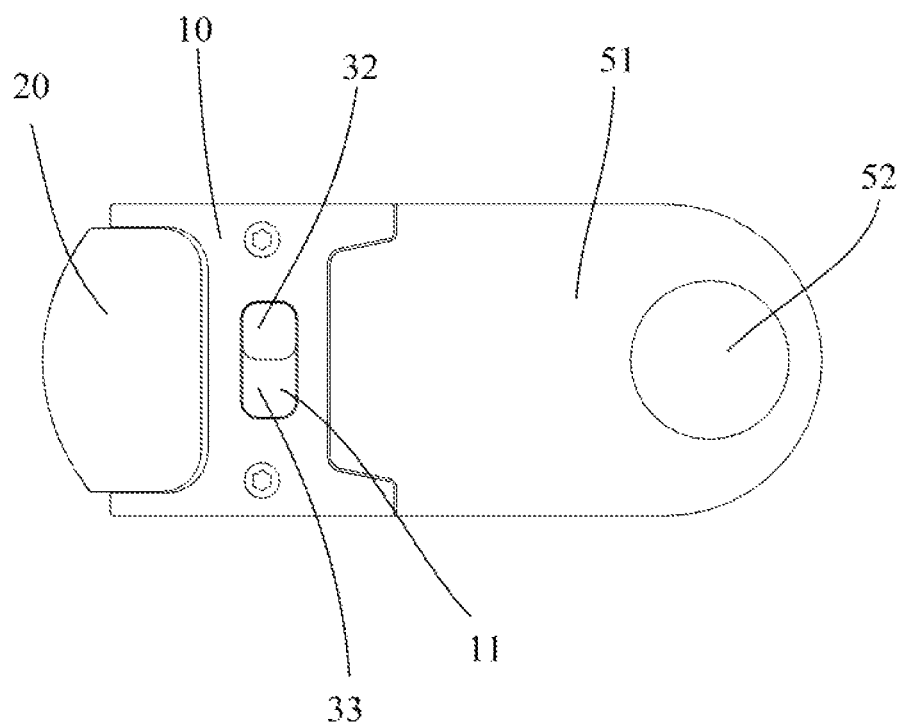
FIG. 3 is a top view of a slide block shown in FIG. 1 located at an unlocking position.
Figure 5:
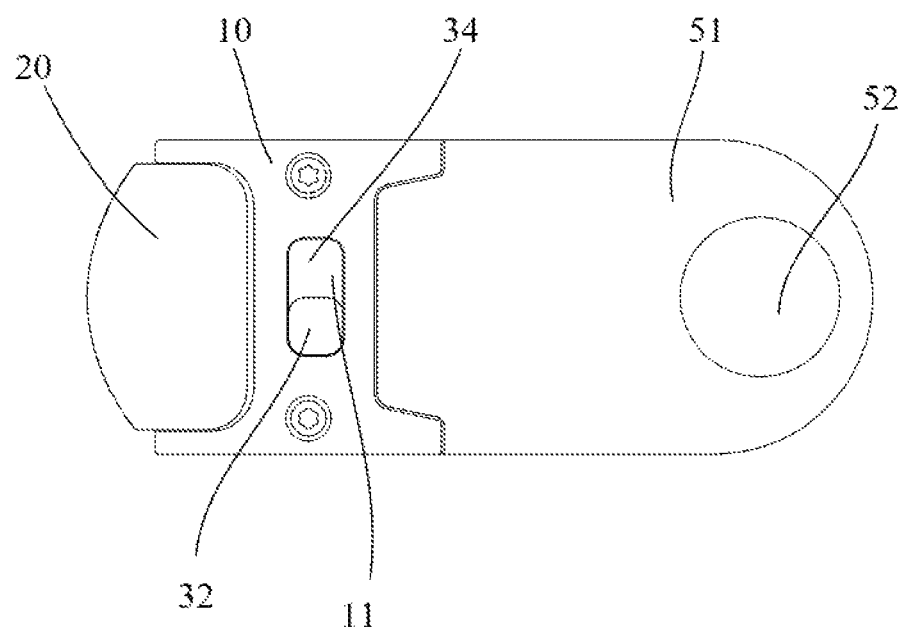
FIG. 5 is a top view of a slide block shown in FIG. 1 located at a locking position.

The slide block 30 is configured to be connected to the support 10 in a sliding manner along a direction perpendicular to the push direction of the push-button 20, and the slide block 30 is capable for sliding and has a locking position 33 and an unlocking position 34 (referring to FIG. 3 and FIG. 5).

The push-button 20 is provided with a first locking portion 21 at one side facing the slide block 30. The slide block 30 is provided with a second locking portion 31 fitting the first locking portion 21.

When the slide block 30 slides to the locking position 33, the first locking portion 21 is locked to the second locking portion 31, so that the push-button 20 is in a locked state; and when the slide block 30 slides to the unlocking position 34, the first locking portion 21 is unlocked from the second locking portion 31, so that the push-button 20 is in an unlocked state.

Figure 4:
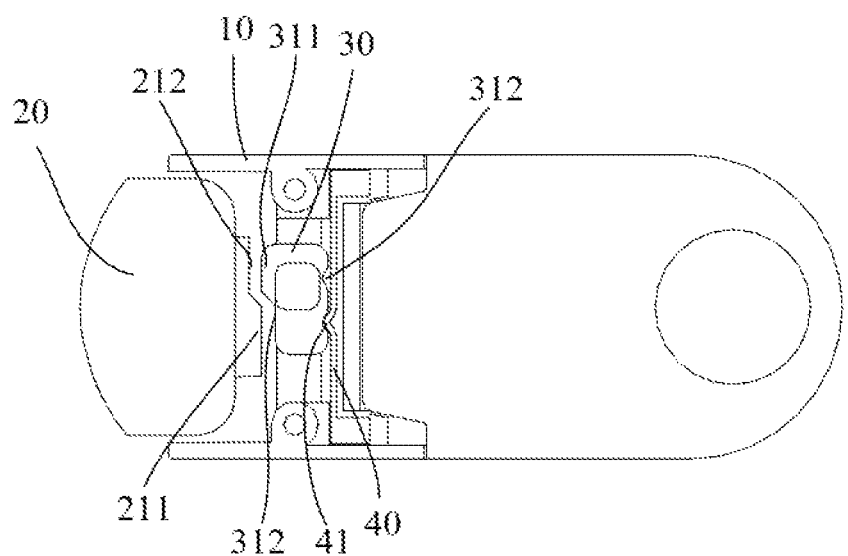
FIG. 4 is a partial cross-sectional view of an electronic atomizer shown in FIG. 3.

Referring to FIG. 4 and FIG. 6, according to the technical scheme of the present disclosure, the slide block 30 of the push-button structure 100 slides relative to the support 10 and has the locking position 33 and the unlocking position 34. The slide block 30 locks and unlocks the push-button 20 when the slide block is located at the locking position 33 and the unlocking position 34 respectively, so that the push-button 20 is in a locked state and an unlocked state. In the unlocked state, the push-button 20 can be used normally. In the locked state, the first locking portion 21 is locked to the second locking portion 31, which makes the push-button 20 and the slide block 30 fixed relative to each other. Since the slide direction of the slide block 30 is perpendicular to the push direction of the push-button 20, the slide block 30 cannot move along the push direction of the push-button 20. At such time, the push-button 20 cannot move either, as a result, the push-button 20 in such state is protected and the occurrence of improper operation is prevented. According to the push-button structure 100, the push-button 20 is capable of switching between the locked state and the unlocked state by toggling the slide block 30 manually. The mechanical operation is simple and reliable and can effectively prevent inconveniences caused by improper operation of the push-button 20.

In the present embodiment, the slide block 30 is arranged at one side the push-button 20 in the push direction. The first locking portion 21 includes a first protrusion portion 211 projecting in the direction towards the slide block 30, and the second locking portion 31 includes a second protrusion portion 311 projecting in the direction towards the push-button 20.

Referring to FIG. 5 and FIG. 6, when the slide block 30 slides to the locking portion 33, the first protrusion portion 211 has an end surface abutted against an end surface of the second protrusion portion 311. Referring to FIG. 3 and FIG. 4, when the slide block 30 slides to the unlocking position 34, the first protrusion portion 211 is staggered from the second protrusion portion 311.

The first locking portion 21 further includes a first abutment surface 212 adjacent to the first protrusion portion 211. The second locking portion 31 further includes a second abutment surface 312 adjacent to the second protrusion portion 311. The first protrusion portion 211 is projected from the first abutment surface 212 in the direction towards the slide block 30. The second protrusion portion 311 is projected from the second abutment surface 312 in the direction towards the push-button 20.

Referring to FIG. 4, when the slide block 30 slides to the unlocking position 34, the first protrusion portion 211 and the second abutment surface 312 are configured to be arranged facing each other and have a gap therebetween, and the second protrusion portion 311 and the first abutment surface 212 are configured to be arranged facing each other and have a gap therebetween. The gap is capable of ensuring the normal push of the push-button 20.

The structure that the first locking portion 21 and the second locking portion 31 are locked to each other is designed as a structure that the first protrusion portion 211 and the second protrusion portion 311 are abutted against each other. The first protrusion portion 211 and the second protrusion portion 311 are simple in structure, have high structural strength and can achieve a good locking effect.

Preferably, in order to improve the comfort of sliding the slide block back and forth between the locking position and the unlocking position, each of the first protrusion portion and the second protrusion portion is provided with an arc transitional surface (not shown in the drawings) configured for connecting one side surface thereof to the end surface thereof. When the slide block slides to the unlocking position, the arc transitional surface of the first protrusion portion and the arc transitional surface of the second protrusion portion are configured to be arranged facing each other.

When the slide block 30 slides to the unlocking position 34, the first protrusion portion 211 and the second protrusion portion 311 are staggered from each other. Both the first protrusion portion and the second protrusion portion are provided with an arc transitional surface at opposing positions. During the process that a user slides the slide block 30 from the unlocking position to the locking position, the arc transitional surface located on the first protrusion portion 211 contacts the arc transitional surface located on the second protrusion portion 311 first. Under the action of the slide fitting of the two arc transitional surfaces, the end surface of the first protrusion portion 211 is easier to reach the end surface of the second protrusion portion 311, so that the use feel is better in the process of sliding the slide block 30 from the unlocking position to the locking position. Likewise, during the process that a user slides the slide block 30 from the locking position to the unlocking position, the user feel is smoother under the action of the slide fitting of the two arc transitional surfaces. The user experience is further improved.

The structure that the first locking portion and the second locking portion are locked to each other can also be designed as a structure in another embodiment (not shown in the drawings) of the present disclosure, besides the structure that the first protrusion portion 211 and the second protrusion portion 311 are abutted against each other. The first locking portion defines an insert groove at one side thereof, and the second locking portion is provided with an insert element fitting the insert groove.

When the slide block slides to the locking position, the insert element is inserted into the insert groove; when the slide block slides to the unlocking position, the insert element is disengaged from the insert groove. Such structure can also allow the slide block to lock and unlock the push-button respectively during the sliding process, and the push-button has a good locking effect in the locked state.

Referring to FIG. 6, in the present embodiment, the slide block 30 defines two locating grooves 313 at one side far away from the second protrusion portion 311, and the two locating grooves 313 are arranged spaced apart from each other along the slide direction of the slide block 30.

Referring to FIG. 4, the support 10 is provided with an elastic locating protrusion 41 fitting the locating groove 313, and the slide block 30 is abutted against the elastic locating protrusion 41 in a sliding manner.

When the slide block 30 slides to the locking position 33, the elastic locating protrusion 41 is accommodated in one locating groove 313; when the slide block 30 slides to the unlocking position 34, the elastic locating protrusion 41 is accommodated in the other locating groove 313.

If the structure that the slide block 30 slides relative to the support 10 and has the locking position 33 and the unlocking position 34 is designed as the structure that the elastic locating protrusion 41 fits the two locating grooves 313, a user can slide the slide block 30 between the locking position 33 and the unlocking position 34 with a slight force, to let the push-button 20 enter the locked state and the unlocked state. When the slide block 30 is at the locking position 33 and the unlocking position 34, the elastic locating protrusion 41 is clamped in one locating groove 313, which achieves a use feel of clamping. Thus, the user has a good use feel when operating the slide block 30, a fool-proof effect is achieved and the user experience is improved.

Referring to FIG. 4 and FIG. 6, the push-button structure 100 further includes an elastic sheet 40 fixed on the support 10, and the elastic sheet 40 is provided with the elastic locating protrusion 41. The elastic sheet 40 is stamped and formed by a precise hardware mould. The elastic sheet 40 is arranged to allow the elastic locating protrusion 41 to be formed thereon, so that the forming mode of the elastic locating protrusion 41 is simple, the structure of the support 10 is simple and the cost of the push-button structure 100 is lowered.

The structure that the slide block slides relative to the support can also be designed as the following structure. In another embodiment (not shown in the drawings) of the present disclosure, the support defines a recess, an elastic element is arranged in the recess, and the elastic element has one end abutted against a bottom wall of the recess and the other end abutted against the elastic locating protrusion. The elastic element can select various common parts having elasticity. In the present embodiment, the elastic element selects a spring preferably, and the elastic locating protrusion selects a steel ball preferably. The elastic locating protrusion can also be a part having one end provided with a curve and the other end inserted into the spring. The end provided with a curve is accommodated in the locating groove, to facilitate the sliding of the slide block. The elastic locating protrusion in this structure can also allow the slide block to reach the locking position and the unlocking position effectively during the process of the slide block sliding relative to the support.

Figure 2:
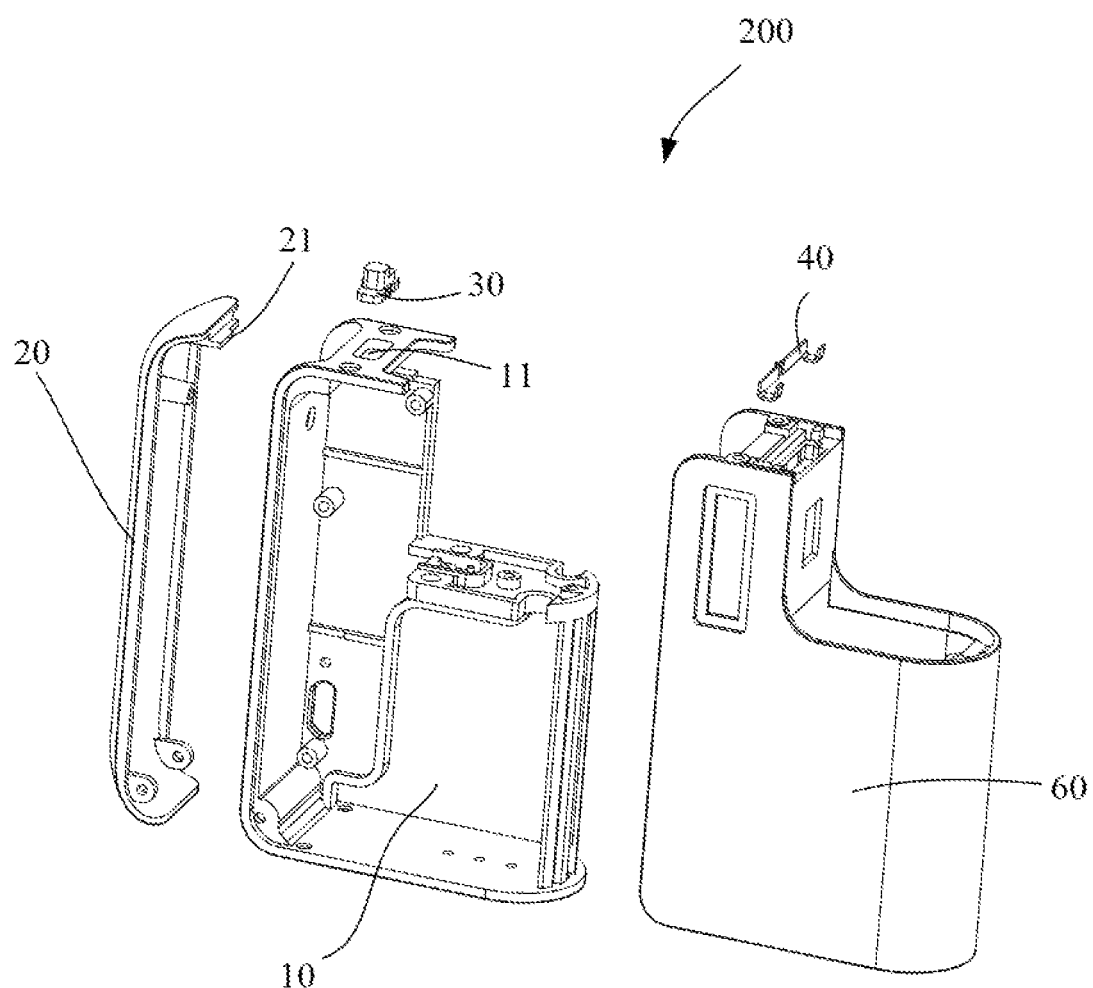
FIG. 2 is an exploded view of a partial structure of the electronic atomizer shown in FIG. 1.

Referring to FIG. 2, in the present embodiment of the present disclosure, the support 10 further defines a mounting hole 11, the slide block 30 is provided with a toggle portion 32, and the toggle portion 32 is configured to extend out the mounting hole 11 and slide relative to the mounting hole 11.

The toggle portion 32 extends out from the mounting hole 11, for a user to operate the slide block 30 conveniently.

The present disclosure further provides an electronic atomizer 200. The electronic atomizer 200 includes the push-button structure 100. The specific structure of the push-button structure 100 can be referred to the above embodiments. Since the present electronic atomizer 200 employs all technical schemes of the above embodiments, the electronic atomizer at least has all the beneficial effects brought by the technical schemes of the above embodiments. No further description is needed here.

Referring to FIG. 1 and FIG. 2, the electronic atomizer 200 includes a mouthpiece assembly 50, a support 10 and a main body 60. The main body 60 is configured to be mounted on the support 10. The mouthpiece assembly 50 includes a mouthpiece base 51 mounted on the main body 60 and a mouthpiece 52 connected to the mouthpiece base 51. The push-button 20 is mounted on one side of the support 10 and covers such side. The push-button 20 has a big size relative to the electronic atomizer 200, so that a user can operate the push-button 20 conveniently. Of course, the push-button 20 can also be designed into other forms, for example, common mechanical buttons.

The support 10 defines a mounting hole 11 at one side adjacent to the push-button 20. The toggle portion 32 of the slide block 30 is configured to extend out the mounting hole 11. In the present embodiment, the mounting hole 11 and the slide block 30 are located at, but are not limited to, one side of the mouthpiece 52. The slide block 30 can be arranged at any position at the peripheral of the push-button 20 to realize the technical effect of the present technical scheme.

Referring to FIG. 1, the push-button 20 is provided with a first locking portion 21 at one end adjacent to the slide block 30. The slide block 30 is provided with a second locking portion 31 at one side facing the push-button 20. The first locking portion 21 and the second locking portion 31 are both covered within the support 10.

The slide block 30 is made of metal materials, so that a user has a good use feel when operating the slide block 30.

The above are preferred embodiments of the present disclosure merely and are not intended to limit the patent scope of the present disclosure. Any equivalent structures made according to the description and the accompanying drawings of the present disclosure without departing from the idea of the present disclosure, or any equivalent structures applied in other relevant technical fields directly or indirectly are intended to be included in the patent protection scope of the present disclosure.

What is claimed is:

1. A push-button structure, comprising:
   a support;
   a push-button, the push-button being connected to the support and having a push direction; and
   a slide block, the slide block being connected to the support in a sliding manner along a direction perpendicular to the push direction of the push-button, and the slide block being capable of sliding and having a locking position and an unlocking position;
   the push-button being provided with a first locking portion at one side facing the slide block; the slide block being provided with a second locking portion fitting the first locking portion;
   when the slide block is located at the locking position, the first locking portion being locked to the second locking portion; and when the slide block is located at the unlocking position, the first locking portion being unlocked from the second locking portion;
   wherein the slide block is arranged at one side the push-button in the push direction;
   the first locking portion comprises a first protrusion portion projecting in the direction towards the slide block, and the second locking portion comprises a second protrusion portion projecting in the direction towards the push-button; and
   when the slide block is located at the locking position, the first protrusion portion has an end surface abutted against an end surface of the second protrusion portion; and when the slide block is located at the unlocking position, the first protrusion portion is staggered from the second protrusion portion;
   wherein the slide block defines two locating grooves at one side far away from the second protrusion portion, and the two locating grooves are arranged spaced apart from each other along a slide direction of the slide block;
   the support is provided with an elastic locating protrusion fitting the locating groove, and the slide block is abutted against the elastic locating protrusion in a sliding manner; and
   when the slide block is located at the locking position, the elastic locating protrusion is accommodated in one locating groove; when the slide block is located at the unlocking position, the elastic locating protrusion is accommodated in the other locating groove.

2. The push-button structure according to claim 1, wherein the push-button structure further comprises an elastic sheet fixed on the support, and the elastic sheet is provided with the elastic locating protrusion.

3. The push-button structure according to claim 1, wherein the support defines a recess, an elastic element is arranged in the recess, the elastic element has one end abutted against a bottom wall of the recess and the other end abutted against the elastic locating protrusion.

4. The push-button structure according to claim 3, wherein the elastic locating protrusion is a steel ball.

5. The push-button structure according to claim 1, wherein each of the first protrusion portion and the second protrusion portion is provided with an arc transitional surface configured for connecting one side surface thereof to the end surface thereof; when the slide block is located at the unlocking position, the arc transitional surface of the first protrusion portion and the arc transitional surface of the second protrusion portion are configured to be arranged facing each other.

6. The push-button structure according to claim 1, wherein the first locking portion defines an insert groove at one side thereof, and the second locking portion is provided with an insert element fitting the insert groove;

when the slide block is located at the locking position, the insert element is inserted into the insert groove; when the slide block is located at the unlocking position, the insert element is disengaged from the insert groove.

7. The push-button structure according to claim 1, wherein the support further defines a mounting hole, the slide block is provided with a toggle portion, and the toggle portion is configured to extend out the mounting hole and slide in the mounting hole.

8. An electronic atomizer, comprising the push-button structure according to claim 1.

* * * * *